United States Patent [19]

Campion et al.

[11] Patent Number: 5,558,631
[45] Date of Patent: *Sep. 24, 1996

[54] TAMPON APPLICATOR

[75] Inventors: Terese A. Campion, Enfield, Conn.; Mark D. Albright, Chichester, England; Betsy A. Davison, Wilbraham, Mass.

[73] Assignee: Tambrands Inc., White Plains, N.Y.

[*] Notice: The term of this patent shall not extend beyond the expiration date of Pat. No. 5,346,468.

[21] Appl. No.: 292,509

[22] Filed: Aug. 18, 1994

Related U.S. Application Data

[63] Continuation of Ser. No. 171,853, Dec. 22, 1993, Pat. No. 5,346,468, which is a continuation of Ser. No. 819,753, Jan. 13, 1992, abandoned.

[51] Int. Cl.⁶ ........................................ A61F 15/00
[52] U.S. Cl. ............................. 604/13; 604/14
[58] Field of Search ........................ 604/11–15, 18, 604/904

[56] References Cited

U.S. PATENT DOCUMENTS

| | | | |
|---|---|---|---|
| 2,013,865 | 9/1935 | Sloan | 18/59 |
| 2,094,268 | 9/1937 | Friedman | 138/78 |
| 2,254,788 | 9/1941 | Ballard | 23/172 |
| 2,489,502 | 11/1949 | Ruth | 128/270 |
| 2,509,241 | 5/1950 | Mende | 128/270 |
| 2,587,717 | 3/1952 | Fourness | 128/263 |
| 3,015,332 | 1/1962 | Brecht | 604/15 |
| 3,148,680 | 9/1964 | Roberts et al. | 604/18 |
| 3,168,982 | 2/1965 | Davis | 239/33 |
| 3,204,635 | 9/1965 | Voss et al. | 128/263 |
| 3,347,234 | 10/1967 | Voss | 604/14 |
| 3,429,312 | 2/1969 | Stump | 604/15 |
| 3,433,225 | 3/1969 | Voss et al. | 128/263 |
| 3,499,447 | 3/1970 | Mattes et al. | 128/285 |
| 3,534,737 | 10/1970 | Jones | 128/263 |
| 3,568,577 | 3/1971 | Voss et al. | 93/77 |
| 3,575,169 | 4/1971 | Voss et al. | 128/263 |
| 3,581,744 | 6/1971 | Voss | 604/14 |
| 3,643,661 | 2/1972 | Crockford | 128/263 |
| 3,674,029 | 7/1972 | Bates et al. | 128/285 |
| 3,683,759 | 8/1972 | Voss et al. | 93/94 |
| 3,696,812 | 10/1972 | Jaycox | 128/263 |

(List continued on next page.)

FOREIGN PATENT DOCUMENTS

| | | |
|---|---|---|
| 630407 | 11/1961 | Canada ............ 604/15 |
| 945703 | 6/1970 | Canada . |
| 1245006 | 11/1988 | Canada . |
| 0613672A1 | 9/1994 | European Pat. Off. . |
| 868718 | 1/1942 | France . |
| 152737 | 12/1969 | New Zealand . |
| 547305 | 8/1942 | United Kingdom . |
| 1108291 | 3/1968 | United Kingdom . |
| 1116742 | 12/1968 | United Kingdom . |
| 1272863 | 4/1969 | United Kingdom . |
| 2097259 | 11/1982 | United Kingdom . |
| 2132484 | 12/1982 | United Kingdom . |
| 2120945 | 12/1983 | United Kingdom . |
| 2133695 | 8/1984 | United Kingdom . |
| 2166656 | 5/1986 | United Kingdom . |
| 2207750 | 6/1988 | United Kingdom . |
| 2202750 | 10/1988 | United Kingdom . |
| 2220359 | 1/1990 | United Kingdom . |
| 9410959 | 5/1994 | WIPO . |

*Primary Examiner*—Randy C. Shay
*Attorney, Agent, or Firm*—Fish & Richardson P.C.

[57] ABSTRACT

An insertion device 10 for inserting material 13 into a body cavity is provided. An elongate, tubular holder 12, shaped for insertion into the body cavity, is adapted to hold the material to be inserted. The holder 12 has a material expulsion end portion 14 and a plunger 20, which is telescopically and slidably mounted in the holder, which is adapted to expel the material from the holder when pushed manually into the holder. The holder, and preferably the plunger as well, comprises an outer paper layer 28 and a polymer layer 30, adhered to the paper layer on its outer surface, the layer having adequate water resistance to maintain its integrity during insertion into the body cavity.

64 Claims, 1 Drawing Sheet

U.S. PATENT DOCUMENTS

| | | | |
|---|---|---|---|
| 3,706,311 | 12/1972 | Kokx et al. | 128/285 |
| 3,724,462 | 4/1973 | Hanke | 128/263 |
| 3,760,808 | 9/1973 | Bleuer | 128/263 |
| 3,830,237 | 8/1974 | Bernardin | 604/359 |
| 4,077,409 | 3/1978 | Murray et al. | 128/285 |
| 4,088,132 | 5/1978 | Wood et al. | 128/285 |
| 4,258,704 | 3/1981 | Hill | 128/1 R |
| 4,271,835 | 6/1981 | Conn et al. | 128/270 |
| 4,273,125 | 6/1981 | Sakurai | 128/263 |
| 4,286,595 | 9/1981 | Ring | 128/263 |
| 4,286,639 | 9/1981 | Murphy | 383/61 |
| 4,287,244 | 9/1981 | McMahon, Jr. et al. | 428/35 |
| 4,291,696 | 9/1981 | Ring | 128/263 |
| 4,312,348 | 1/1982 | Friese | 128/263 |
| 4,361,151 | 11/1982 | Fitzgerald | 128/285 |
| 4,372,311 | 2/1983 | Potts | 128/287 |
| 4,412,833 | 11/1983 | Wiegner | 604/14 |
| 4,453,925 | 6/1984 | Decker | 604/14 |
| 4,496,341 | 1/1985 | Brucks | 604/14 |
| 4,508,531 | 4/1985 | Whitehead | 604/14 |
| 4,536,178 | 8/1985 | Lichstein et al. | 604/15 |
| 4,543,086 | 9/1985 | Johnson | 604/11 |
| 4,553,965 | 11/1985 | Conn et al. | 604/286 |
| 4,622,030 | 11/1986 | Sheldon et al. | 604/15 |
| 4,626,238 | 12/1986 | Sustmann | 604/15 |
| 4,650,459 | 3/1987 | Sheldon | 604/15 |
| 4,792,326 | 12/1988 | Tews | 604/11 |
| 4,846,802 | 7/1989 | Sanders, III | 604/15 |
| 4,848,363 | 7/1989 | Cattanach | 128/834 |
| 4,857,044 | 8/1989 | Lennon | 604/14 |
| 4,891,042 | 1/1990 | Melvin et al. | 604/18 |
| 4,973,302 | 11/1990 | Armour et al. | 604/15 |
| 5,000,315 | 3/1991 | Butler | 206/229 |
| 5,002,526 | 3/1991 | Herring | 604/11 |
| 5,041,080 | 8/1991 | Shimatani et al. | 604/13 |
| 5,087,239 | 2/1992 | Beastall et al. | 604/14 |
| 5,135,475 | 8/1992 | Nakanishi et al. | 604/14 |
| 5,230,939 | 7/1993 | Baum | 428/84 |
| 5,279,541 | 1/1994 | Frayman et al. | 604/14 |
| 5,346,468 | 9/1994 | Campion et al. | 604/13 |

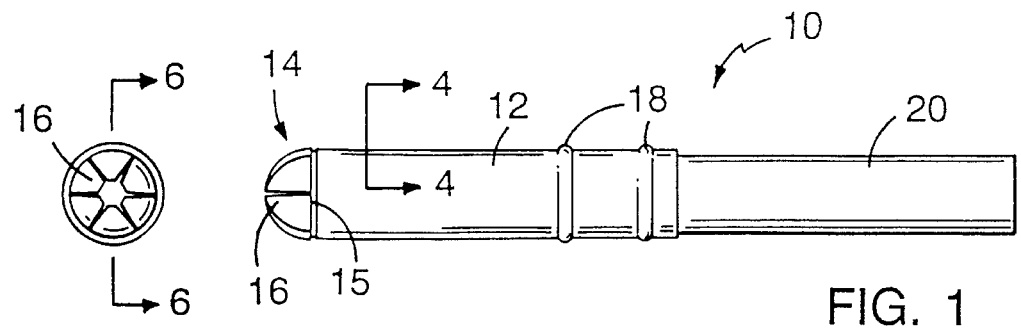
FIG. 1
FIG. 2
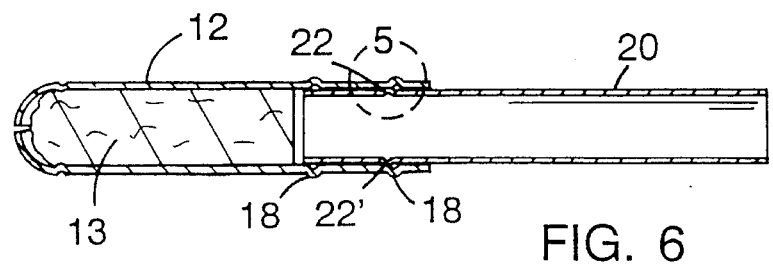
FIG. 6
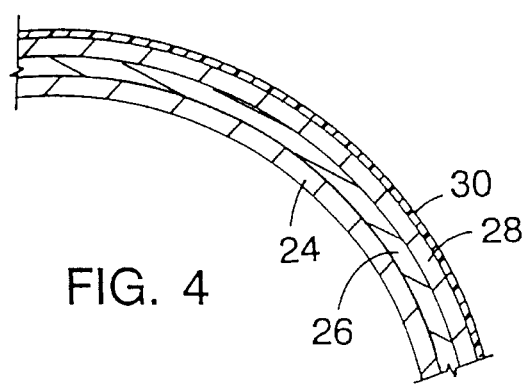
FIG. 4
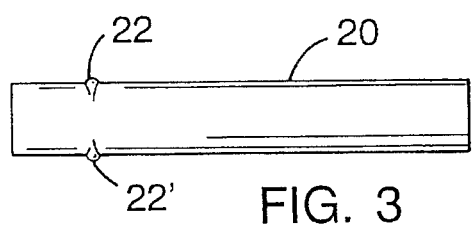
FIG. 3
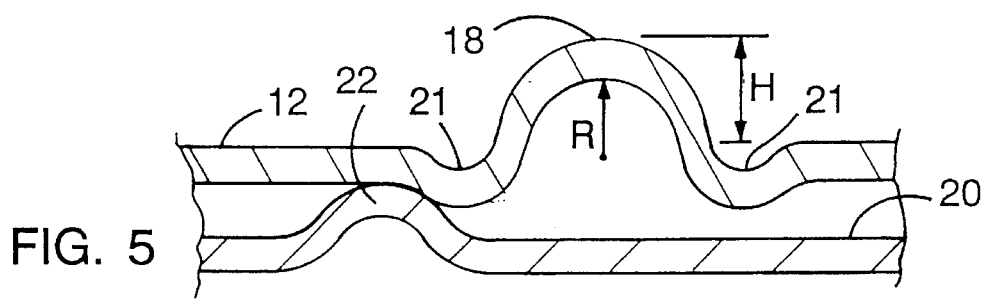
FIG. 5
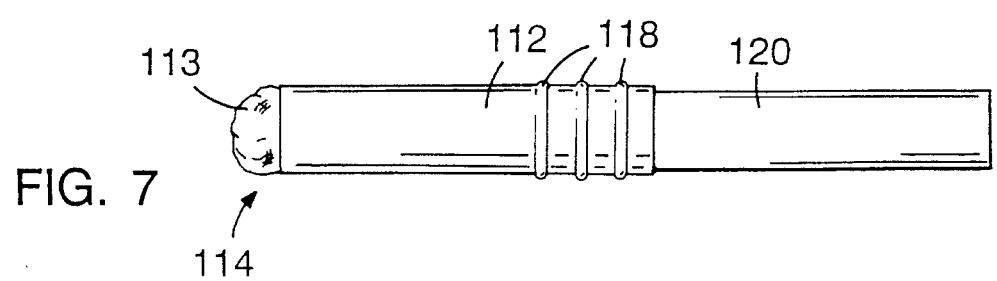
FIG. 7

5,558,631

1

TAMPON APPLICATOR

CROSS-REFERENCE TO RELATED APPLICATIONS

This application is a continuation of U.S. Ser. No. 08/171,853, filed Dec. 22, 1993, now U.S. Pat. No. 5,346,468, which was a continuation of U.S. Ser. No. 07/819,753, filed Jan. 13, 1992, now abandoned.

BACKGROUND OF THE INVENTION

The invention relates to an insertion device, e.g. a tampon applicator, formed from a paper laminate.

Tampon applicators comprising a pair of telescopically arranged tubes are long known in the art. Some applicators have the tampon exposed at the end intended for vaginal insertion (the expulsion end). Others provide a rounded expulsion end, with the tampon covered by a plurality of "petals" which open during tampon expulsion.

Properties considered when selecting a material for the applicator include slip characteristics of the outer sheet material's surface, for ease and comfort of the user during insertion of applicator, water resistance, flushability, delamination, biodegradability and aesthetic appearance.

Applicators have long been manufactured by spirally winding a number of paper layers about a mandrel, gluing each layer to the previous one to form a tubular shape. One such applicator comprises two adjacent layers of ground wood paper and an outer layer of bleached Kraft paper, coated with a wax/clay coating. Known advantages of such laminated paper applicators are their ability to delaminate when exposed to water, thus making them flushable, and their greater biodegradability.

Paper, however, is inferior to plastics in tampon applicators in several respects. Plastics have better slip characteristics and a glossier, more aesthetic appearance than conventional paper products. Additionally, it is difficult to form raised or indented areas in a paper tube without cracking, splitting or shearing, whereas plastic can easily be molded to a desired shape.

SUMMARY OF THE INVENTION

We have discovered that a laminated paper insertion device, comprising telescopically disposed applicator tubes, can be greatly improved in a variety of respects by adhering a layer of polymer (selected from cellophane, polyethylene, polyester, polypropylene, polycaprolactone and ethylene vinyl acetate) to the exterior surface of one or more of the applicator tubes, and providing the polymer with moisture resistance. The moisture-resistant polymer provides improved slip characteristics, for ease of insertion and greater user comfort, and a more aesthetically pleasing product, all without loss of flushability (i.e., its ability to delaminate when placed in water). In preferred embodiments, the paper layer immediately beneath the polymer is a white paper, that works in conjunction with the smooth surface provided by the polymer to provide the aesthetic appearance of the product. The improvement in appearance of the paper surface is such that the appearance approaches that of plastic applicators in smoothness and sheen.

The insertion tube of the invention is suitable for use in a variety of applications, e.g. as a tampon applicator, or a device for the application of suppositories, creams or the like to the vaginal area or other body cavities.

2

It is also preferred to use the new polymer layer on the exterior surface of the inner tube, or plunger, of the applicator, for its use in that location reduces friction between the plunger and the outer tube of the applicator. Reduced friction between the tubes has been found to be important, for when the outer tube is squeezed tightly during insertion significant frictional forces can develop between the plunger and outer tube, thus increasing insertion force.

In another aspect of the invention, improved rings are embossed in a paper laminate applicator by adhering a polymer layer to the underlying paper material, and then embossing the laminated polymer/paper material. The polymer is selected from the group consisting of cellophane films, polyethylene films, polypropylene films, polyester films, polycaprolactone films and ethylene vinyl acetate films. The improved embossed rings have much greater definition than has been provided in conventional paper-laminate applicators. Preferably, the radius of curvature of the embossed rings is less than about 0.060 inches, more preferably less than about 0.055 inches, and most preferably less than about 0.050 inches, and the height of the rings is preferably at least 0.010 inches, and more preferably at least 0.015 inches. The improved rings can be used to form a more positive finger grip on the exterior of the applicator and/or improved retention formations on the inner and outer tubes for preventing the tubes from inadvertently being separated during use.

The invention can provide embossed formations (e.g., rings) that, if attempted in conventional paper applications, would tend to rip, shear, or otherwise damage the laminated paper. The invention permits outwardly embossed rings to be formed on the applicator tubes, something not conventionally found in paper applicators, and improves the overall ability of the paper to be worked, i.e. formed into petals, grooves and the like.

BRIEF DESCRIPTION OF THE DRAWINGS

FIG. 1 is a side view of a tampon applicator according to one embodiment of the invention.

FIG. 2 is a front view of the applicator of FIG. 1, showing the petal-type expulsion end.

FIG. 3 is a side view of the inner tube, or plunger, of the applicator shown in FIG. 1.

FIG. 4 is a partial cross-sectional view of the applicator of FIG. 1, taken along line 4—4.

FIG. 5 is a highly enlarged, fragmentary view of detail 5 in FIG. 1.

FIG. 6 is a cross-sectional side view of the applicator of FIG. 1.

FIG. 7 is a side view of a tampon applicator according to another embodiment of the invention.

DESCRIPTION OF THE PREFERRED EMBODIMENTS

An applicator according to a preferred embodiment of the invention is shown in FIGS. 1–6. The applicator comprises tubular tampon holder 12 and plunger 20, telescopically and slidably mounted in holder 12. Tampon 13 is retained within tampon holder 12. Tampon holder 12 has two embossed rings 18 disposed circumferentially around its surface, distal to expulsion end 14. Expulsion end 14 comprises a plurality of petals 16. Preferably, a preformed hinge or groove 15 is disposed circumferentially at the base of the petals. Plunger 20 comprises nibs 22, which interlock with the inner surface of either of rings 18, to resist inadvertent separation of the plunger from the tampon holder. Interlocking is assisted by the interference fit (approximately 0.002 inches interference is preferred) between the nibs and a slight depression 21 which is formed on either side of the embossed ring during embossing. (See FIG. 5) While nibs 22 are shown, these could be replaced by raised areas of any desired shape, including continuous raised rings, provided the interlocking function is provided. Depressions 21 are typically formed inherently by the embossing process. However, if these depressions are not formed, or not desired, interlocking could be provided by an interference fit between the tampon holder and plunger which would cause nibs 22 to snap into rings 18 and interlock therewith.

FIG. 4 illustrates, in cross-section, the layers of which tampon holder 12 is comprised: ground wood paper inner layers 24 and 26, bleached Kraft outer paper layer 28, and cellophane layer 30 disposed on the outer tube surface. Each of the layers is adhered to adjoining layers by adhesive, preferably a water-based adhesive, to allow the layers to delaminate when the applicator is exposed to water, thereby permitting the applicator to be disposed of by flushing. The water-based adhesive also preserves the biodegradability of the product. Suitable adhesives include, for example, dextrin and polyvinyl acetate, with polyvinyl acetate being preferred for its ability to resist delamination under humid storage conditions. Suitable polyvinyl acetate adhesives are commercially available from Findley Adhesives, Wauwatosa, Wis.

It is preferred that both the tampon holder and the plunger have the illustrated construction, although the plunger may be of a different material, e.g. plastic or wax-coated paper, if desired.

FIG. 7 illustrates another type of tampon applicator in which the construction of the invention may be utilized. In this embodiment of the invention, tampon holder 112 is of the open-end type, such that tampon head 113 extends beyond the expulsion end of the holder tube. Three embossed rings 118 are provided to assure a positive grip.

While two types of applicators have been shown in FIGS. 1 and 7, the construction of the invention is useful in many types of applicators, including, e.g., closed-end compact and open-end regular applicators.

The cellophane layer may be of any grade of cellophane so long as it has adequate water resistance to maintain its integrity and remain tack-free when used in the invention, i.e. adequate to withstand humid environments for long periods of time, and to withstand insertion into the vagina, without becoming tacky or dissolving. Accordingly, the term does not refer to pure regenerated cellulose which is free from any additives or coatings, for such material has extremely low water resistance. Suitable cellophanes may contain additives or surface coatings which impart water resistance, with surface coatings being preferred. Preferred water resistant coatings are selected from the group consisting of nitrocellulose and polyvinylidene chloride, with nitrocellulose preferred for its biodegradability. A nitrocellulose coated cellophane sheet is commercially available from Flexel, Inc., Atlanta, Ga. Water resistance is typically measured in terms of Water Vapor Transmission Rate (WVTR). It is preferred that the cellophane film have a WVTR of less than about 100 g/m$^2$/day.

It is preferred that the cellophane layer be thin relative to the paper layer. Preferably the thickness is less than about 0.0020 inches, more preferably less than 0.0009 inches.

It is preferred, for aesthetic reasons, that the outer paper layer be a white paper. Although any conventional white paper may be used, it is preferred that the paper be selected from the group consisting of bleached Kraft paper and bleached sulfite paper. If no other paper layer is to be utilized, the white paper will be selected to have adequate rigidity to provide structural strength to the finished tube for its use as a tampon applicator. The paper may contain additional optical brighteners, e.g. stilbene derivatives, and the like to enhance the aesthetic appearance of the laminate. The brighteners, and overall whiteness of the paper, work in conjunction with the gloss of the cellophane layer to greatly improve the aesthetic appearance of the resulting applicator. Preferred thicknesses for the outer paper layer are in the range of 0.0015 to 0.005 inches, more preferably 0.003 inches.

Because most papers have relatively low rigidity, multiple layers are preferably employed in both the tampon holder and plunger. Accordingly, in addition to the outer paper layer, it is preferred that the applicator further comprise at least one inner paper layer. It is preferred that each inner paper layer be an inexpensive, durable paper, e.g. ground wood paper. It is further preferred that two inner paper layers be provided. Preferred thicknesses for the inner paper layers are in the range of 0.002 to 0,007 inches for each layer, more preferably 0.00625 inches.

Other polymers may be used in place of cellophane, although with loss of some of the unique advantages of cellophane for this application. A variety of thermoplastic polymers may be used. The polymers should be capable of being formed into a relatively thin sheet, and be themselves water-resistant or have a coating or additive which imparts water-resistance. Preferred polymers include but are not limited to cellophane, polyethylene, polyester, polypropylene, polycaprolactone, and ethylene vinyl acetate.

Any conventional process can be used to form the tube, e.g. spiral or convolute winding of the individual layers, each layer on top of the previous layer about a common central axis. Spiral winding is generally preferred. It is also preferred that the seams formed in each layer during spiral winding be offset from the seams in other layers. These methods are well known to those skilled in the art.

It is preferred that the embossed rings in the tampon holder be formed by embossing. While any conventional embossing technique can be utilized, a preferred method is to support the tubular tampon holder on a spinning central mandrel having circumferential ridges in its surface, and contact the surface of the tampon holder with a pair of rolling dies having indentations corresponding in shape to the ridges on the mandrel. It is also preferred that heat be employed during the embossing process to render the cellophane layer more malleable and thus enhance the formability of the paper.

It is preferred that the embossed formations be in the form of rings around the circumference of the tampon holder, as illustrated in the figures. Preferably, the radius of curvature of the rings (R in FIG. 5) is less than about 0.060 inches, more preferably less than about 0.055 inches, and most preferably less than about 0.050 inches. The height of the rings (H in FIG. 5) is preferably at least 0.010 inches, and more preferably at least 0.015 inches.

While preferred embodiments have been described above, other variations and modifications are within the scope of the following claims.

For example, the outer paper layer need not be white. Colored paper may be utilized, if desired, provided the paper is compatible with the adhesive used to bond the layers together. Different numbers of gripping rings may be used, or the rings may be replaced with other embossed formations, e.g. dots, longitudinal ridges or ribs of varying dimensions.

We claim:

1. An insertion device for inserting a tampon material into the vagina comprising:

an elongate, tubular holder shaped for insertion into the vagina, adapted to hold the tampon to be inserted, and having an expulsion end portion; and a plunger, telescopically and slidably mounted in said holder distal to said expulsion end and adapted to expel said tampon from said holder when pushed manually into said holder;

wherein said holder comprises an outer polymer film layer adhered to an outer surface of an underlying paper layer, and the polymer film layer having an outer surface and an inner surface, substantially all of the area of said inner surface being supported by and adhered to said outer surface of said underlying paper layer, said polymer film layer comprising a polymer selected from the group consisting of cellophane, polypropylene, polyester, polycaprolactone, and ethylene vinyl acetate, and having a WVTR of less than 100 g/m$^2$/day, so that the polymer layer has adequate water resistance to maintain its integrity during insertion into the body cavity, said polymer film being capable of separation from said underlying paper layer as an intact, self-supporting layer.

2. The device of claim 1 wherein said polymer film layer comprises polyester.

3. The device of claim 1 or 2 wherein said plunger comprises an outer paper layer to which is adhered a polymer film layer, said polymer film layer being adhered to said paper on its outer surface, and said polymer film layer comprising a polymer selected from the group consisting of cellophane, polypropylene, polycaprolactone, polyester, and ethylene vinyl acetate.

4. The device of claim 1 or 2 wherein said underlying paper layer and said polymer film layer are spirally wound about a common central axis.

5. The device of claim 1 or 2 wherein said underlying paper layer and said polymer film layer are convolutely wound about a common central axis.

6. The device of claim 1 wherein there is a single said outer polymer film layer over an underlying paper layer.

7. The device of claim 6 wherein the inner surface of the single outer polymer film layer is adhered directly by adhesive to the underlying paper layer.

8. The tampon applicator of claim 1 wherein said polymer film layer is adhered to said underlying paper layer by at least one intermediate layer.

9. The tampon applicator of claim 8 wherein said intermediate layer comprises an adhesive.

10. The tampon applicator of claim 9 wherein there is a single polymer film layer adhered by said adhesive to said underlying paper layer.

11. The tampon applicator of claim 10 wherein said adhesive comprises a material that loses adhesion when said device is immersed in water, so that when said device is immersed in water said polymer film layer separates from said underlying paper layer.

12. The tampon applicator of claim 1 wherein said polymer film layer is adhered to said underlying paper layer in such a manner that when said device is immersed in water said polymer film layer separates from said underlying paper layer.

13. A tampon applicator comprising:

an elongate tubular holder shaped for vaginal insertion, adapted to contain a tampon, and having an expulsion end portion and a gripping end portion distal the expulsion end portion, and at least one raised formation at the gripping end portion to form a finger grip for said holder, said raised formation being unitary with said holder; and a plunger, telescopically and slidably mounted in said holder at said gripping end and adapted to expel said tampon from said holder when pushed manually into said holder;

wherein said holder comprises an outer polymer film layer adhered to an outer surface of an underlying paper layer, said polymer film layer comprising a polymer selected from the group consisting of cellophane, polyethylene, polypropylene, polyester, polycaprolactone and ethylene vinyl acetate, said polymer film layer being capable of separation from said underlying paper layer as an intact, self-supporting layer.

14. The tampon applicator of claim 13 wherein the outer surface of said holder is intact and free from rips in the area of said raised formation.

15. The tampon applicator of claim 13 wherein said raised formation is embossed.

16. A tampon applicator comprising:

an elongate tubular holder shaped for vaginal insertion, adapted to contain a tampon, and having an expulsion end portion and a gripping end portion distal the expulsion end portion, and at least one deformation at the gripping end portion to form a finger grip for said holder, said deformation being unitary with said holder; and a plunger, telescopically and slidably mounted in said holder at said gripping end and adapted to expel said tampon from said holder when pushed manually into said holder;

wherein said holder comprises an outer polymer film layer adhered to an outer surface of an underlying paper layer, said polymer film layer being capable of separation from said underlying paper layer as an intact, self-supporting layer.

17. The tampon applicator of claim 16 wherein said polymer film layer comprises a polymer selected from the group consisting of cellophane, polyethylene, polypropylene, polyester, polycaprolactone and ethylene vinyl acetate.

18. The tampon applicator of claim 16 wherein said deformation extends radially outward, away from the longitudinal axis of said holder tube.

19. The tampon applicator of claim 16 wherein the outer surface of said holder is intact and free from rips in the area of said deformation.

20. The tampon applicator of claim 16 wherein said deformation is embossed.

21. The tampon applicator of claim 16 wherein said deformation is an outwardly embossed deformation that extends radially outward, away from the longitudinal axis of said holder tube, and the outer surface of said holder is intact and free from rips in the area of said deformation.

22. The tampon applicator of claim 16 wherein said polymer film layer is bonded to said underlying paper layer by a single intermediate layer.

23. The tampon applicator of claim 22 wherein said single intermediate layer comprises an adhesive.

24. The tampon applicator of claim 23 wherein there is a single polymer film layer adhered by said adhesive to said underlying paper layer.

25. The tampon applicator of claim 1, 13, 16, or 21 wherein the outer surface of the polymer film layer has sheen.

26. The tampon applicator of claim 1, 13, 16, or 21 wherein said expulsion end portion is rounded and comprises a plurality of petals which separate during expulsion.

27. An insertion device for inserting a tampon material into the vagina, said device comprising an elongate, tubular holder shaped for insertion into the vagina, adapted to hold the tampon to be inserted, and having an expulsion end portion; and a plunger, telescopically and slidably mounted in said holder distal to said expulsion end and adapted to expel said tampon from said holder when pushed manually into said holder;

wherein said holder has been made by a method comprising the step of adhering a self-supporting polymer film layer to an outer surface of an underlying paper layer, the polymer film layer having an inner surface, substantially all of the area of said inner surface being supported by and adhered to said outer surface of said underlying paper layer, said polymer film layer comprising a polymer selected from the group consisting of cellophane, polypropylene, polyester, polycaprolactone, and ethylene vinyl acetate, and having a WVTR of less than 100 g/m$^2$/day, so that the polymer layer has adequate water resistance to maintain its integrity during insertion into the body cavity.

28. The device of claim 27 wherein said polymer film layer comprises polyester.

29. The device of claim 27 or 28 wherein said plunger comprises an outer paper layer to which is laminated a polymer film layer, said polymer film layer being laminated to said paper on its outer surface, and said polymer film layer comprising a polymer selected from the group consisting of cellophane, polypropylene, polycaprolactone, polyester, and ethylene vinyl acetate.

30. The device of claim 27 or 28 wherein said underlying paper layer and said polymer film layer are spirally wound about a common central axis.

31. The device of claim 27 or 28 wherein said underlying paper layer and said polymer film layer are convolutely wound about a common central axis.

32. The device of claim 27 wherein said expulsion end portion is rounded and comprises a plurality of petals which separate during expulsion.

33. The device of claim 27 wherein there is a single said outer polymer film layer over an underlying paper layer.

34. The device of claim 33 wherein the inner surface of the single outer polymer film layer is adhered directly by adhesive to the underlying paper layer.

35. The tampon applicator of claim 27 wherein said polymer film layer is adhered to said underlying paper layer by at least one intermediate layer.

36. The tampon applicator of claim 35 wherein said intermediate layer comprises an adhesive.

37. The tampon applicator of claim 36 wherein there is a single polymer film layer adhered by said adhesive to said underlying paper layer.

38. The tampon applicator of claim 36 wherein said adhesive comprises a material that loses adhesion when said device is immersed in water, so that when said device is immersed in water said polymer film layer separates from said underlying paper layer.

39. The tampon applicator of claim 27 wherein said polymer film layer is adhered to said underlying paper layer in such a manner that when said device is immersed in water said polymer film layer separates from said underlying paper layer.

40. A tampon applicator comprising:

an elongate tubular holder shaped for vaginal insertion, adapted to contain a tampon, and having an expulsion end portion and a gripping end portion distal the expulsion end portion, and at least one raised formation at the gripping end portion to form a finger grip for said holder, said raised formation being unitary with said holder; and a plunger, telescopically and slidably mounted in said holder at said gripping end and adapted to expel said tampon from said holder when pushed manually into said holder;

wherein said holder has been made by a method comprising the step of adhering a self-supporting polymer film layer to an outer surface of an underlying paper layer, said polymer film layer comprising a polymer selected from the group consisting of cellophane, polyethylene, polypropylene, polyester, polycaprolactone and ethylene vinyl acetate.

41. The tampon applicator of claim 40 wherein the outer surface of said holder is intact and free from rips in the area of said raised formation.

42. The tampon applicator of claim 40 wherein said raised formation is embossed.

43. A tampon applicator comprising:

an elongate tubular holder shaped for vaginal insertion, adapted to contain a tampon, and having an expulsion end portion and a gripping end portion distal the expulsion end portion, and at least one deformation at the gripping end portion to form a finger grip for said holder, said deformation being unitary with said holder; and a plunger, telescopically and slidably mounted in said holder at said gripping end and adapted to expel said tampon from said holder when pushed manually into said holder;

wherein said holder has been made by a method comprising the step of adhering a self-supporting polymer film layer to an outer surface of an underlying paper layer.

44. The tampon applicator of claim 43 wherein said polymer film layer comprises a polymer selected from the group consisting of cellophane, polyethylene, polypropylene, polyester, polycaprolactone and ethylene vinyl acetate.

45. The tampon applicator of claim 43 wherein said deformation extends radially outward, away from the longitudinal axis of said holder tube.

46. The tampon applicator of claim 43 wherein the outer surface of said holder is intact and free from rips in the area of said deformation.

47. The tampon applicator of claim 43 wherein said deformation is embossed.

48. The tampon applicator of claim 43 wherein said deformation is an outwardly embossed deformation that extends radially outward, away from the longitudinal axis of said holder tube, and the outer surface of said holder is intact and free from rips in the area of said deformation.

49. The tampon applicator of claim 43 wherein said polymer film layer is bonded to said underlying paper layer by a single intermediate layer.

50. The tampon applicator of claim 49 wherein said single intermediate layer comprises an adhesive.

51. The tampon applicator of claim 50 wherein there is a single polymer film layer adhered by said adhesive to said underlying paper layer.

52. The tampon applicator of claim 27, 40, 43, or 48 wherein the outer surface of the polymer film layer has sheen.

53. The tampon applicator of claim 27, 40, 43, or 48 wherein said expulsion end is rounded and comprises a plurality of petals which separate during expulsion.

54. An insertion device for inserting a tampon material into the vagina comprising:

an elongate, tubular holder shaped for insertion into the vagina, adapted to hold the tampon to be inserted, and having an expulsion end portion; and a plunger, telescopically and slidably mounted in said holder distal to said expulsion end and adapted to expel said tampon from said holder when pushed manually into said holder;

wherein said holder comprises an outer polymer film layer adhered by an intermediate layer to an outer surface of an underlying paper layer, and the polymer film layer having an outer surface and an inner surface, substantially all of the area of said inner surface being supported by and adhered to said outer surface of said underlying paper layer, said polymer film layer comprising a polymer selected from the group consisting of cellophane, polypropylene, polyester, polycaprolactone, and ethylene vinyl acetate, and having a WVTR of less than 100 g/m$^2$/day, so that the polymer layer has adequate water resistance to maintain its integrity during insertion into the body cavity.

55. A tampon applicator comprising:

an elongate tubular holder shaped for vaginal insertion, adapted to contain a tampon, and having an expulsion end portion and a gripping end portion distal the expulsion end portion, and at least one raised formation at the gripping end portion to form a finger grip for said holder, said raised formation being unitary with said holder; and a plunger, telescopically and slidably mounted in said holder at said gripping end and adapted to expel said tampon from said holder when pushed manually into said holder;

wherein said holder comprises an outer polymer film layer adhered by an intermediate layer to an outer surface of an underlying paper layer, said polymer film layer comprising a polymer selected from the group consisting of cellophane, polyethylene, polypropylene, polyester, polycaprolactone and ethylene vinyl acetate.

56. A tampon applicator comprising:

an elongate tubular holder shaped for vaginal insertion, adapted to contain a tampon, and having an expulsion end portion and a gripping end portion distal the expulsion end portion, and at least one deformation at the gripping end portion to form a finger grip for said holder, said deformation being unitary with said holder; and a plunger, telescopically and slidably mounted in said holder at said gripping end and adapted to expel said tampon from said holder when pushed manually into said holder;

wherein said holder comprises an outer polymer film layer adhered by an intermediate layer to an outer surface of an underlying paper layer.

57. The tampon applicator of claim 56 wherein said polymer film layer comprises a polymer selected from the group consisting of cellophane, polyethylene, polypropylene, polyester, polycaprolactone and ethylene vinyl acetate.

58. The tampon applicator of claim 56 wherein said deformation extends radially outward, away from the longitudinal axis of said holder tube.

59. The tampon applicator of claim 56 wherein the outer surface of said holder is intact and free from rips in the area of said deformation.

60. The tampon applicator of claim 56 wherein said deformation is an outwardly embossed deformation that extends radially outward, away from the longitudinal axis of said holder tube, and the outer surface of said holder is intact and free from rips in the area of said deformation.

61. The tampon applicator of claim 54, 55, or 56 wherein said single intermediate layer comprises an adhesive.

62. The tampon applicator of claim 61 wherein there is a single polymer film layer adhered by said adhesive to said underlying paper layer.

63. The tampon applicator of claims 54, 55, or 56 wherein the outer surface of the polymer film layer has sheen.

64. The tampon applicator of claim 54, 55, or 56 wherein said expulsion end portion is rounded and comprises a plurality of petals which separate during expulsion.

* * * * *